(12) United States Patent
Schneider et al.

(10) Patent No.: US 10,379,022 B2
(45) Date of Patent: Aug. 13, 2019

(54) AIR-MASS MEASURING APPARATUS, AIR-MASS MEASURING SYSTEM AND AIR-MASS MEASURING METHOD FOR A VEHICLE

(71) Applicant: Robert Bosch GmbH, Stuttgart (DE)

(72) Inventors: Norbert Schneider, Tiefenbronn (DE); Michael Horstbrink, Stuttgart (DE); Uwe Konzelmann, Asperg (DE); Andreas Kuehn, Ettlingen (DE); Michael Rittmann, Ditzingen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 25 days.

(21) Appl. No.: 15/105,330

(22) PCT Filed: Nov. 4, 2014

(86) PCT No.: PCT/EP2014/073697
§ 371 (c)(1),
(2) Date: Jun. 16, 2016

(87) PCT Pub. No.: WO2015/090713
PCT Pub. Date: Jun. 25, 2015

(65) Prior Publication Data
US 2016/0313227 A1 Oct. 27, 2016

(30) Foreign Application Priority Data
Dec. 17, 2013 (DE) ........................ 10 2013 226 140

(51) Int. Cl.
*G01N 9/00* (2006.01)
*G01F 1/684* (2006.01)
(Continued)

(52) U.S. Cl.
CPC ............. *G01N 9/00* (2013.01); *G01F 1/6842* (2013.01); *G01F 1/696* (2013.01); *G01F 15/022* (2013.01);
(Continued)

(58) Field of Classification Search
CPC .... G01N 9/00; G01N 33/0004; G01F 1/6842; G01F 1/696; G01F 15/022; G01F 15/043;
(Continued)

(56) References Cited

U.S. PATENT DOCUMENTS 4,467,769 A * 8/1984 Matsumura ......... F02D 41/0032
123/520
4,561,302 A * 12/1985 Sumal ................... G01F 1/6842
73/114.34
(Continued)

FOREIGN PATENT DOCUMENTS

CN 1740531 A 3/2006
DE 19750496 5/1999
(Continued)

OTHER PUBLICATIONS

International Search Report dated Jan. 26, 2015, of the corresponding International Application PCT/EP2014/073697, filed on Nov. 4, 2014.

*Primary Examiner* — Marrit Eyassu
(74) *Attorney, Agent, or Firm* — Norton Rose Fulbright US LLP; Gerard Messina

(57) ABSTRACT

An air-mass measuring apparatus for a vehicle, that has a support element, an air-mass sensor for providing air-mass data, the air-mass sensor being disposed on the support element, at least one further sensor for providing further sensor data, the at least one further sensor being disposed on the support element, and an evaluation circuit having a first input interface to receive the air-mass data, at least one
(Continued)

second input interface to receive the further sensor data and having an output interface, the evaluation circuit being disposed on the support element and being designed to provide the air-mass data and the further sensor data as bundled sensor data via the output interface.

14 Claims, 3 Drawing Sheets

(51) Int. Cl.
- *G01K 13/02* (2006.01)
- *G01F 1/696* (2006.01)
- *G01F 15/02* (2006.01)
- *G01F 15/04* (2006.01)
- *G01N 33/00* (2006.01)

(52) U.S. Cl.
CPC .......... *G01F 15/043* (2013.01); *G01K 13/02* (2013.01); *G01N 33/0004* (2013.01); *G01K 2013/024* (2013.01); *G01K 2201/02* (2013.01)

(58) Field of Classification Search
CPC ............ G01K 13/02; G01K 2013/024; G01K 2201/02
USPC .................. 73/30.01, 202.5, 204.11–204.27, 73/861.42–861.68
See application file for complete search history.

(56) References Cited

U.S. PATENT DOCUMENTS

| | | | | |
|---|---|---|---|---|
| 4,586,479 | A * | 5/1986 | Isomura | F02D 41/062 123/478 |
| 6,494,090 | B1 * | 12/2002 | Losing | G01F 1/6842 73/204.26 |
| 6,581,447 | B1 * | 6/2003 | Strohrmann | F02D 41/18 73/114.31 |
| 6,591,675 | B1 * | 7/2003 | Doderer | G01F 1/6842 73/204.22 |
| 7,269,999 | B2 * | 9/2007 | Nakano | G01F 1/6842 73/202.5 |
| 2004/0250610 | A1 | 12/2004 | Dempsey et al. | |
| 2009/0056410 | A1 * | 3/2009 | Ricks | G01F 1/6845 73/1.34 |
| 2011/0259097 | A1 * | 10/2011 | Mais | G01D 11/245 73/204.25 |
| 2012/0048005 | A1 * | 3/2012 | Renninger | G01F 1/6842 73/114.32 |
| 2017/0167744 | A1 * | 6/2017 | Arensmeier | F04D 25/06 |

FOREIGN PATENT DOCUMENTS

| | | |
|---|---|---|
| DE | 102010043062 | 5/2012 |
| EP | 1637847 | 3/2006 |
| WO | 2007031516 A1 | 3/2007 |

* cited by examiner

AIR-MASS MEASURING APPARATUS, AIR-MASS MEASURING SYSTEM AND AIR-MASS MEASURING METHOD FOR A VEHICLE

BACKGROUND INFORMATION

The present invention relates to an air-mass measuring apparatus, an air-mass measuring system and an air-mass measuring method for a vehicle, which may be used, for example, to measure air mass in a combustion engine of a vehicle.

The measuring of air mass is established in the case of gasoline engines and diesel engines. It is used to regulate the fuel-injection quantity and the exhaust-gas recirculation.

SUMMARY

Against this background, the present invention introduces an air-mass measuring apparatus, an air-mass measuring system and an air-mass measuring method for a vehicle. Advantageous refinements are described below.

In addition to the air mass, at least one physical variable is advantageously able to be detected by an air-mass measuring apparatus. The data acquired may be forwarded in bundled fashion via a connection. In comparison to an unbundled transmission, the number of lines necessary for transmitting the acquired data may be reduced.

Even though air is discussed in the specific embodiments and exemplary embodiments, the air-mass measuring apparatus may be used to measure the mass of any gas or gas mixture. The practical application in the vehicle sector is also selected only by way of example.

An air-mass measuring apparatus for a vehicle has the following features:
 a support element;
 an air-mass sensor for providing air-mass data, the air-mass sensor being disposed on the support element;
 at least one further sensor for providing further sensor data, the at least one further sensor being disposed on the support element; and
 an evaluation circuit having a first input interface to receive the air-mass data, at least one second input interface to receive the further sensor data, and having an output interface, the evaluation circuit being disposed on the support element and being designed to provide the air-mass data and the further sensor data as bundled sensor data via the output interface.

For example, the air-mass measuring apparatus may be used to ascertain an air mass supplied to a combustion engine of a vehicle. The air-mass measuring apparatus may be implemented, for instance, as what is referred to as an integrated pressure- and humidity sensor. For example, the data provided by the evaluation circuit at the output interface may be received by a control unit of the vehicle and further processed. The support element may be formed to be placed in an electronics chamber of a housing. The further sensor may be designed to detect a further physical parameter of the air, whose mass is sensed by the air-mass sensor. The evaluation circuit may be realized as an integrated circuit. The at least one sensor may include a signal-conditioning device for conditioning acquired sensor values and may be designed to transmit the sensor data as conditioned data to the evaluation circuit. The evaluation circuit may be designed to bundle the data, received via the input interfaces, according to a communications protocol of the output interface to form the bundled sensor data. For example, the bundled data may be made available at the output interface at the same time or staggered over time.

According to one specific embodiment, the air-mass measuring apparatus may have a humidity sensor, and additionally or alternatively, a pressure sensor as the at least one further sensor. In this way, a humidity, as well as a pressure of the air may be detected together with the mass of the air.

Additionally or alternatively, the air-mass measuring apparatus may have a temperature sensor. The temperature sensor may be connected to the support element via a sensor interface of the support element. Thus, for example, a thermal detector of the temperature sensor may be disposed adjacent to the support element. Therefore, in addition to the mass, the temperature of the air may also be detected.

The evaluation circuit may have the second input interface to receive humidity data provided by a humidity sensor, a third input interface to receive pressure data provided by a pressure sensor and a fourth input interface to receive temperature data provided by a temperature sensor. The evaluation circuit may be designed to provide the air-mass data, the humidity data, the pressure data and the temperature data in bundled form via the output interface. In this context, it is not necessary that all sensors indicated here be implemented. In this way, great flexibility is provided. For instance, different functional variants with additional temperature-, pressure- or humidity measurement are feasible.

The output interface of the evaluation circuit may be three-wire. For example, the evaluation circuit may be connected to a supply voltage and to ground via the connections of the output interface. A signal voltage for representing the bundled sensor data may be transmitted via the third connection. For instance, the signal voltage may represent an amplitude-modulated or frequency-modulated signal. Such an output interface may be implemented as a SENT (Single Edge Nibble Transmission) interface, for example. The output interface may take the form of a digital interface that permits a digital signal transmission, e.g., to a control unit.

The support element may have a sensor carrier and a printed circuit board. The air-mass sensor may be disposed on the sensor carrier. The at least one further sensor and the evaluation circuit may be disposed on the printed circuit board. The air-mass sensor or the sensor carrier may be connected to the evaluation circuit via electric lines. The electronics module may have a base element on which the sensor carrier and the printed circuit board are mounted. For instance, such a base element may be a plate. The base element, the sensor carrier and the printed circuit board may be joined rigidly to each other. The base element may be used to secure the electronics module to a housing. To that end, the electronics module may have a fastening interface for fastening the electronics module to a housing.

The evaluation circuit and the at least one further sensor may be disposed on the same side of the printed circuit board. This facilitates the populating of the printed circuit board.

Accordingly, the air-mass measuring apparatus may include a housing. The housing may have an electronics chamber, a measuring channel for conducting a gas and an electrical connection. The electronics module may be disposed in the electronics chamber. The air-mass sensor may be inserted into the measuring channel. The output interface of the evaluation circuit may be connected via electric lines to the electrical connection, in order to make the bundled sensor data available at the electrical connection. The connection may represent an external interface of the air-mass measuring apparatus. For instance, the housing may take the form of a plug-in sensor housing. The gas, e.g., air, whose mass is to be determined, may be conducted through the measuring channel. In this way, the air-mass measuring apparatus may represent a compact unit.

An air-mass measuring system for a vehicle has an air-mass measuring apparatus disposed or able to be disposed in an induction tract of a combustion engine of a vehicle. In this context, the air-mass measuring apparatus is connected or is connectable via the electrical connection to a control unit of the vehicle. Thus, the air-mass measuring apparatus indicated is suited advantageously for use in a motor vehicle, e.g., an automobile or a truck.

An air-mass measuring method for a vehicle includes the following steps:

Reception of air-mass data via a first input interface of an evaluation circuit disposed on a support element, the air-mass data representing data provided by an air-mass sensor disposed on the support element;

Reception of further sensor data via at least one second input interface of the evaluation circuit, the further sensor data representing data provided by at least one further sensor disposed on the support element; and Provision of the air-mass data and the further sensor data as bundled sensor data via an output interface of the evaluation circuit.

The above-mentioned steps may be implemented advantageously using devices of the indicated air-mass measuring apparatus.

BRIEF DESCRIPTION OF THE DRAWINGS

Below, the present invention is explained in detail by way of example with reference to the figures.

DETAILED DESCRIPTION OF EXAMPLE EMBODIMENTS

In the following description of preferred exemplary embodiments of the present invention, the same or similar reference symbols are used for the similarly functioning elements shown in the various figures, a repeated description of these elements being omitted.

Figure 1:
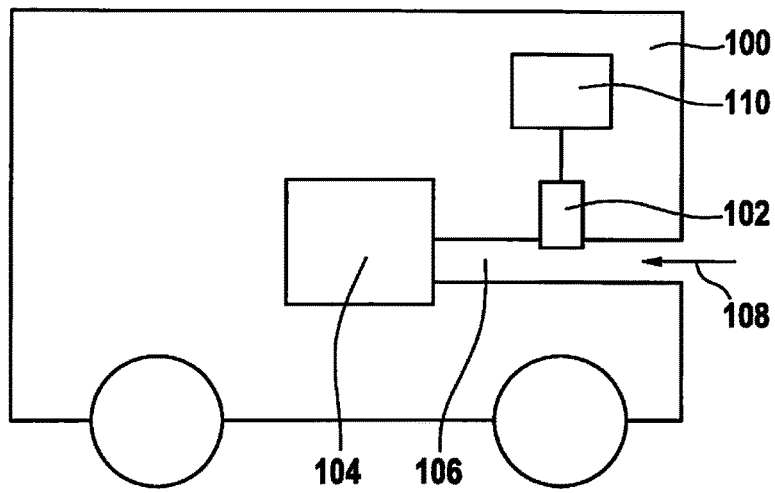
FIG. 1 shows a schematic representation of a vehicle having an air-mass measuring apparatus.

FIG. 1 shows a schematic representation of a vehicle 100 having an air-mass measuring apparatus 102 according to one exemplary embodiment of the present invention. Vehicle 100 has a combustion engine 104 to which air 108 is supplied via an air duct 106. Air-mass measuring apparatus 102 is disposed in or on air duct 106, and is designed to acquire a value representing an air mass of air 108 and, according to this exemplary embodiment, to make it available to a control unit 110 of vehicle 100.

According to different exemplary embodiments, air-mass measuring apparatus 102 may also be designed to acquire values representing a temperature, a pressure and/or a humidity of air 108, and to make them available as joint data together with the value representing the air mass.

Figure 2:
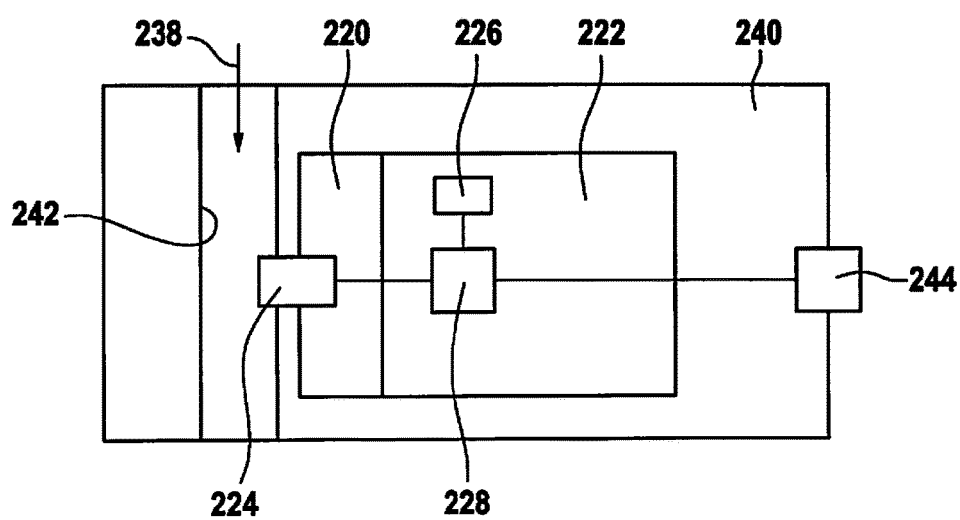
FIG. 2 shows a schematic representation of an air-mass measuring apparatus.

FIG. 2 shows a schematic representation of an air-mass measuring apparatus 102 according to one exemplary embodiment of the present invention. Air-mass measuring apparatus 102 has a support element. The support element may be in one piece or, as shown in FIG. 2, may include a sensor carrier 220 and a printed circuit board 222 that are joined mechanically to each other.

An air-mass sensor 224 is disposed on sensor carrier 220. At least one further sensor 226 and an evaluation circuit 228 are situated on printed circuit board 222. According to this exemplary embodiment, further sensor 226 and evaluation circuit 228 are disposed on the same upper face of printed circuit board 222.

Air-mass sensor 224 is designed to provide air-mass data with regard to an air-mass flow 238. Air-mass sensor 224 is designed to provide the air-mass data via electric lines to evaluation circuit 228.

The at least one further sensor 226 is designed to acquire further sensor data with regard to air-mass flow 238, e.g., a temperature, a humidity or a pressure of air-mass flow 238, and to make it available via electric lines to evaluation circuit 228.

According to this exemplary embodiment, for each sensor 224, 226, evaluation circuit 228 has an input interface for receiving the respective sensor data of sensors 224, 226. Evaluation circuit 228 also has an output interface. Evaluation circuit 228 is designed to receive the air-mass data of air-mass sensor 224 and the further sensor data of the at least one further sensor 226 via separate interfaces, and to provide it as bundled sensor data via the joint output interface. For example, the output interface may have one line or a pair of lines, via which both signals representing the air-mass data and signals representing the further sensor data may be transmitted. To that end, evaluation circuit 228 may be designed to combine the air-mass data and the further sensor data with each other according to a communications protocol of the output interface.

According to one exemplary embodiment, air-mass measuring apparatus 102 may be regarded as an electronics module that may be disposed in a housing 240.

Alternatively, as shown in FIG. 2, air-mass measuring apparatus 102 may be conceived of as a module that has housing 240 with an electronics chamber, in which sensor carrier 220 with air-mass sensor 224, and printed circuit board 222 with further sensor 226 and evaluation circuit 228 are situated. Housing 240 has a measuring channel 242 for conducting mass flow 238. Air-mass sensor 224 may be inserted into measuring channel 242. Housing 240 has an electrical connection 244 as external interface, via which air-mass measuring apparatus 102 may be connected to a control unit, for instance. Electrical connection 244 is connected to the output interface of evaluation circuit 228 via electric lines. A communications protocol of data transmitted via electrical connection 244 may correspond to a communications protocol of the output interface.

Figure 3:
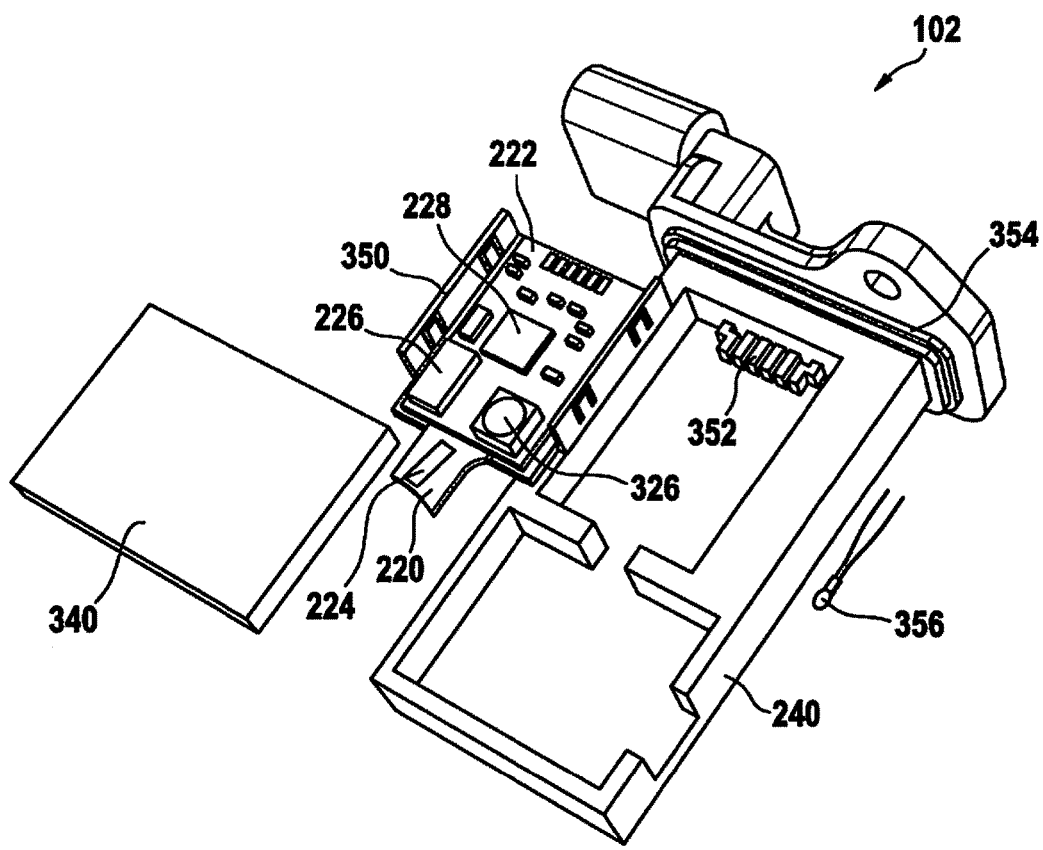
FIG. 3 shows a representation of devices of an air-mass measuring apparatus.

FIG. 3 shows a representation of devices of an air-mass measuring apparatus 102 according to one exemplary embodiment of the present invention. Air-measuring apparatus 102 according to this exemplary embodiment takes the form of a plug-in sensor, especially a plug-in pressure-, humidity- and temperature sensor.

An electronics module is shown, that has a sensor carrier 220 for an air-mass sensor and a printed circuit board 222 having an evaluation circuit 228 and, according to this exemplary embodiment, two further sensors 226, 326. Evaluation circuit 228 is implemented as an evaluation IC. For example, further sensor 226 is realized as a pressure sensor, e.g., a solderable pressure sensor, and further sensor 326 is realized as a humidity sensor that includes, e.g., a semi-permeable membrane having a measuring-chamber humidity sensor and a humidity sensor. The electronics module also includes a base plate 350. A side of printed circuit board 222 facing away from sensors 226, 326 and evaluation circuit 228 lies on a bottom of base plate 350. Base plate 350 has two facing wall sections that are at right angles to the bottom of base plate 350 and run along two opposite edges of printed circuit board 222. The wall sections of base plate 350 have fasteners, e.g., through holes and/or locking hooks, to secure base plate 350 to a housing 240 of air-mass measuring apparatus 102. Sensor carrier 220 protrudes beyond a free end of printed circuit board 222, which is not shielded by any wall section of base plate 350. Sensor carrier 220 is situated approximately centrally with respect to the free end of printed circuit board 222. Sensor carrier 220 is approximately half as wide as printed circuit board 222. Main surfaces of sensor carrier 220 and of the printed circuit board are aligned generally parallel to each other.

Housing 240 has an electronics chamber for accommodating the electronics module. Adjacent to the electronics chamber, housing 240 has a measuring channel. The measuring channel is formed by a measuring-channel section of housing 240 and by a further housing part 340 that is mounted as a measuring-channel (bypass-) cover on the measuring-channel section of housing 240. The measuring channel has a multitude of bends to guide a gas through the housing of air-mass measuring apparatus 102. Once the electronics module is situated in the electronics chamber, sensor carrier 220 extends into the measuring channel. In this way, the air-mass sensor disposed on sensor carrier 220 may be in direct contact with gas conducted through the measuring channel.

The electronics chamber may be covered by a further cover. It may be an electronics-compartment cover. A connection of pressure sensor 326 and humidity sensor 356 may be shielded with respect to the surroundings by the electronics-compartment cover.

Housing 240 has a conductor comb 352. Conductor comb 352 has a plurality of electrical conductors. Printed circuit board 222 and especially evaluation circuit 228 may be connected via conductor comb 352 to an electrical connection of air-mass measuring apparatus 102 located on housing 240.

A circumferential sealing ring 354 may be disposed on housing 240. For example, if air-mass measuring apparatus 102 is inserted into an air duct 106 with the section of housing 240 having the measuring channel first, then an outer wall of the air duct, through which air-mass measuring apparatus 102 is guided, may be sealed by sealing ring 354. At the same time, the connection of air-mass measuring apparatus 102 may be located outside of the air duct.

According to this exemplary embodiment, air-mass measuring apparatus 102 has a further sensor in the form of a thermal detector 356. Thermal detector 356 may be disposed adjacent to printed circuit board 222, for example. Connections of thermal detector 356 may be contacted via conductor comb 352.

Sensors 226, 326, 356 may be referred to as sensor satellites.

According to one exemplary embodiment, air-mass measuring apparatus 102 is realized as an air-mass sensor 102 with an integration of pressure- and humidity sensor 226, 326 in a plug-in sensor with digital SENT interface.

In the case of air-mass sensor 102 (integrated pressure- and humidity sensor), in addition to air mass and intake-air temperature, further measured quantities are ascertained, such as pressure, relative humidity and temperature at humidity sensor 326. The individual sensors 226, 326, 356 for pressure, air mass, humidity and temperature operate independently of each other. The respective measured quantities are in each case transmitted via a separate line to evaluation circuit 228.

Because of the joint output interface of evaluation circuit 228, an 8-pin plug is not necessary on housing 240 of air-mass sensor 102; rather, a 3-pin plug is sufficient, for example. Moreover, it is not necessary to have two electronics chambers on the front side and back side of the plug-in sensor; rather, a single electronics chamber is adequate. Both the electronics for the air-mass measurement and the electronics for pressure measurement and humidity measurement are in the shared electronics chamber. The electronics for the air-mass measurement and also the assembly of pressure sensor 226 and humidity module 356 may be accomplished on a production line.

For instance, the air-mass sensor may take the form of a micromechanical sensor.

The approach described here makes it possible to realize a flexible, cost-effective integration of pressure- and humidity sensor systems 226, 326 with only one evaluation circuit 228, and to transmit the measurement data via one signal line, e.g., to the control unit.

By the integration of pressure- and humidity sensors 226, 326 on the electronics module of air-mass sensor 102, the production line necessary till now for the assembly of pressure sensor 226 and humidity sensor 326 may be omitted completely. At the same time, the number of components required may be reduced considerably. For example, this relates to the elimination of a further printed circuit board for a humidity module or of a microcontroller. The elimination of a second electronics chamber permits the use of a smaller plug-in-sensor housing 240 with reduced overall dimensions and improved functionality, e.g., in terms of a pressure drop.

By the link-up of sensor satellites 226, 326 with evaluation IC 228 of air-mass sensor (HFM) (hot-film air mass flow sensor) 102, all sensor signals may be transmitted via one signal line to the control unit. The costs, e.g., for a cable harness of a vehicle, may thereby be reduced considerably owing to the decrease in the number of plug pins of the connection of air-mass sensor 102, e.g., from 8 to 3.

Air-mass sensor 102 (pressure, temperature, humidity) has an electronics chamber. The electronics chamber is used to accommodate the electronics module. The electronics module is made up of base plate 350 with integrally extruded sensor carrier 220. Sensor carrier 220 is used to accommodate the sensor for measuring air mass. A printed circuit board 222 fitted with components is mounted on base plate 350. According to one exemplary embodiment, printed circuit board 222 is joined to the sensor for measuring air mass with the aid of fine-wire bonds. All electrical components 226, 228, 326, with the exception of thermal detector 356, are mounted and soldered on printed circuit board 222 by a standard SMD process. The fitting is carried out in repeated pattern, that is, on a plurality of printed circuit boards 222 simultaneously. Variants, e.g., without pressure sensor 226, may be embodied relatively easily and cost-effectively by the SMD assembly process.

Humidity sensor 326 sits in what is referred to as a measuring chamber, whose opening is closed by a semi-permeable membrane. It is permeable for humidity, but at the same time protects humidity sensor 326 from penetrating water and dirt.

Pressure sensor and humidity sensor 226, 326 function as independent sensors on printed circuit board 222. That is to say, measuring and signal conditioning are carried out in respective sensors 226, 326 themselves. Thermal detector 356 is linked up with evaluation circuit 228 of air-mass sensor 102 via conductor comb 352 and heavy-wire bonds between conductor comb 352 and printed circuit board 222.

Figure 4:
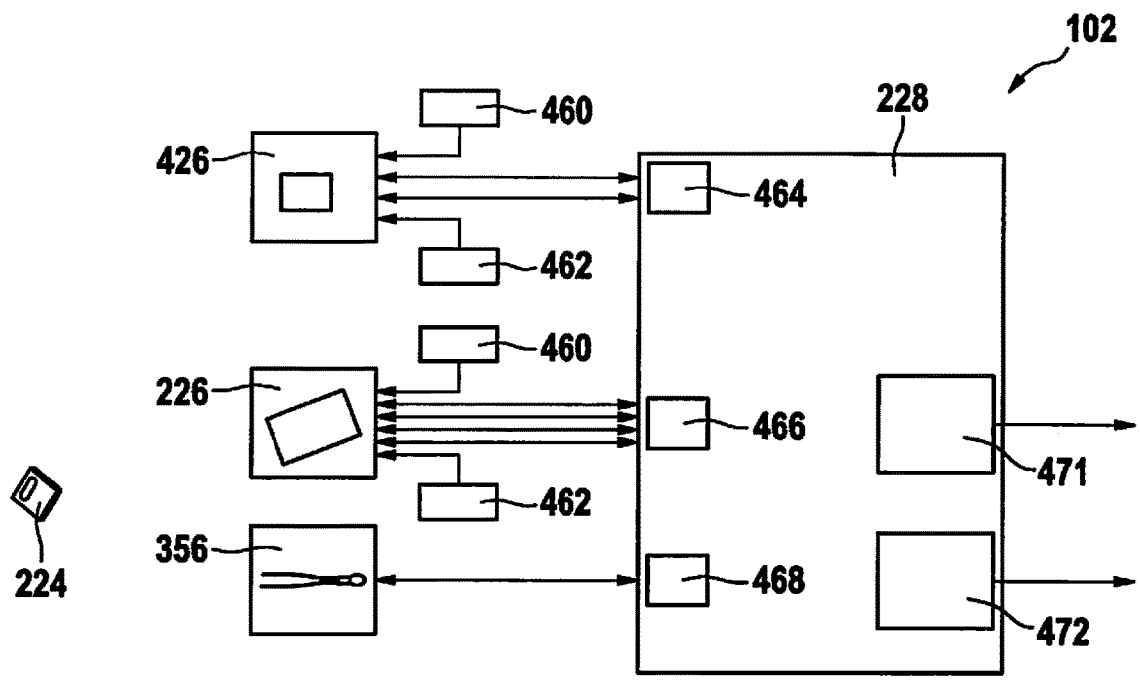
FIG. 4 shows a block diagram of an air-mass measuring apparatus.

By using a digital SENT interface, all sensor signals may be transmitted via one signal line to the control unit. To that end, additional sensors 226, 326, 356 for pressure, temperature and humidity are linked as satellites to evaluation IC 228 of air-mass sensor 102, as shown in FIG. 4. This evaluation IC 228 collects the measurement data, conditions it and sends it via a SENT interface, e.g., to the control unit.

FIG. 4 shows a block diagram of an air-mass measuring apparatus 102 according to one exemplary embodiment of the present invention. In particular, a link-up of sensor satellites 226, 326, 356, as they are depicted with the aid of FIG. 3, for example, with evaluation circuit 228 is shown.

As described with reference to FIG. 3, the sensor satellites may be a humidity sensor 426, a pressure sensor 226 and a temperature sensor 356.

According to this exemplary embodiment, humidity sensor 426 has a connection to a supply voltage (VSupply) 460, a connection to ground (GND) 462 and two bidirectional connections for connecting humidity sensor 426 to a first input interface 464 of evaluation circuit 228. Humidity sensor 426 according to this exemplary embodiment is connected to evaluation circuit 228 via a serial data bus. In this exemplary embodiment, first input interface 464 is realized as an I2C (inter-integrated circuit) interface.

According to this exemplary embodiment, pressure sensor 226 has a connection to a supply voltage (VSupply) 460, a connection to ground (GND) 462 and four bidirectional connections for connecting pressure sensor 226 to a second input interface 466 of evaluation circuit 228. In this exemplary embodiment, pressure sensor 226 is connected to evaluation circuit 228 via a synchronous serial data bus. Second input interface 466 according to this exemplary embodiment is realized as an SPI (serial peripheral interface) interface.

According to this exemplary embodiment, temperature sensor 356 has a connection for connecting temperature sensor 356 to a third input interface 468 of evaluation circuit 228. In this exemplary embodiment, temperature sensor 356 is connected to evaluation circuit 228 via an analog connection. Third input interface 468 according to this exemplary embodiment takes the form of an analog-to-digital converter.

In this exemplary embodiment, evaluation circuit 228 is realized as an integrated evaluation circuit in the form of an ASIC. The evaluation circuit has a first output interface 471 and a second output interface 472. First output interface 471 according to this exemplary embodiment is implemented as a SENT interface or as a frequency interface. Second output interface 472 in this exemplary embodiment is realized as a frequency interface.

According to one exemplary embodiment, evaluation circuit 228 is designed to combine the sensor data received via input interfaces 464, 466, 468, and optionally, in addition the sensor data of an air-mass sensor 224, which may be coupled to evaluation circuit 228 via a further input interface, and to output the sensor data via first output interface 471 realized as joint interface.

Figure 5:
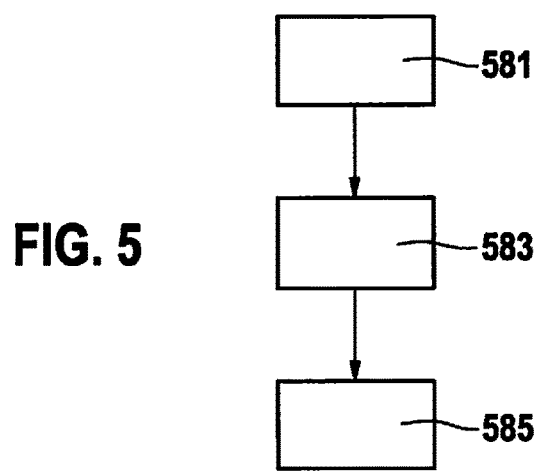
FIG. 5 shows a flowchart of an air-mass measuring method.

FIG. 5 shows a flowchart of an air-mass measuring method according to one exemplary embodiment of the present invention. For example, the method may be carried out using an air-mass measuring apparatus as shown in the previous figures.

In a step 581, air-mass data is received via a first input interface of an evaluation circuit disposed on a support element. The air-mass data may be provided by an air-mass sensor situated on the support element.

In a step 583, further sensor data is received via at least one second input interface of the evaluation circuit. The further sensor data may be provided by at least one further sensor disposed on the support element.

In a step 585, bundled sensor data is output or made available via an output interface of the evaluation circuit. The bundled sensor data includes both the air-mass data and the further sensor data. After being received by the evaluation circuit, the air-mass data as well as the further sensor data may be stored temporarily in order to be able to integrate it into a communications protocol of the output interface.

The exemplary embodiments described and illustrated in the figures are selected only by way of example. Different exemplary embodiments may be combined with each other completely or in terms of individual features. One exemplary embodiment may also be supplemented by features from another exemplary embodiment.

Moreover, method steps according to the present invention may be repeated, as well as executed in a sequence other than that described.

If an exemplary embodiment includes an "and/or" link between a first feature and a second feature, this is to be read in such a way that the exemplary embodiment according to one specific embodiment has both the first feature and the second feature, and according to a further specific embodiment, has either only the first feature or only the second feature.

What is claimed is:

1. An air-mass measuring apparatus for a vehicle, comprising:
a support element;
an air-mass sensor for providing air-mass data, the air-mass sensor being disposed on the support element;
at least one further sensor for providing further sensor data, the at least one further sensor being disposed on the support element; and
an evaluation circuit having a first input interface to receive the air-mass data, at least one second input interface to receive the further sensor data, and an output interface that includes a first wire connected to a source power voltage, a second wire connected to ground, and a third single shared data output wire, the evaluation circuit being disposed on the support element and being designed to provide the air-mass data and the further sensor data as bundled sensor data via the output interface by storing the air-mass data and the further sensor data and processing the stored air-mass data and the stored further sensor data to convert them into an integrated data element of a communications protocol, which is transmitted over the third shared single data output wire;
wherein the integrated data element is transmitted as a signal voltage representing an amplitude-modulated or frequency modulated signal.

2. The air-mass measuring apparatus as recited in claim 1, wherein the at least one further sensor includes at least one of a humidity sensor and a pressure sensor.

3. The air-mass measuring apparatus as recited in claim 1, further comprising:
a temperature sensor connected to the support element via a sensor interface of the support element.

4. The air-mass measuring apparatus as recited in claim 1, wherein the evaluation circuit has the second input interface to receive humidity data provided by a humidity sensor, a third input interface to receive pressure data provided by a pressure sensor and a fourth input interface to receive temperature data provided by a temperature sensor, and wherein the evaluation circuit is designed to provide the air-mass data, the humidity data, the pressure data and the temperature data in bundled fashion via the output interface.

5. The air-mass measuring apparatus as recited in claim 1, wherein the support element has a sensor carrier and a printed circuit board, the air-mass sensor being disposed on the sensor carrier, and the at least one further sensor and the evaluation circuit are disposed on the printed circuit board.

6. The air-mass measuring apparatus as recited in claim 5, wherein the evaluation circuit and the at least one further sensor are situated on the same side of the printed circuit board.

7. The air-mass measuring apparatus as recited in claim 1, further comprising:
a housing that has an electronics chamber and a measuring channel for conducting a gas; and
an electrical connection;
wherein the support element is disposed in the electronics chamber, the air-mass sensor being inserted into the measuring channel, and the output interface is connected to the electrical connection via electric lines to make the bundled sensor data available at the electrical connection.

8. The air-mass measuring apparatus as recited in claim 1, further comprising:
a cover;
a base plate; and
a housing that includes an electronics chamber and a measuring channel.

9. The air-mass measuring apparatus as recited in claim 8, wherein:
the housing includes a wall that separates between the electronics chamber and the measuring channel and in there is a cut out,
the support element includes a circuit board and a sensor carrier attached to the circuit board, and
the base plate includes a support surface and side walls extending at right angles from the support surface and including holes or locking hooks by which the base plate is fastened to walls of the electronics chamber of the housing.

10. The air-mass measuring apparatus as recited in claim 9, wherein:
the support element extends through the cut out from the electronics chamber to the measuring channel,
the air-mass sensor is positioned on the support element and is exposed to an environment in the measuring channel, and
the at least one further sensor data and the evaluation circuit are supported on the circuit board in the electronics chamber.

11. The air-mass measuring apparatus as recited in claim 10, wherein:
the cover covers the measuring chamber, and the at least one further sensor is isolated from the measuring chamber by the housing wall and the cover, and
an exterior portion of the wall of the housing that is in the measuring chamber includes a cut out via which a fluid in an air duct of the vehicle can enter the measuring chamber when the air-mass measuring apparatus is installed in the air duct.

12. The air-mass measuring apparatus as recited in claim 11, wherein the housing further includes a circumferential sealing ring at a side of the electronics chamber opposite the measuring chamber, so that, when the air-mass measuring apparatus is inserted into the air duct, the housing with its sealing ring seals an environment outside of the air-mass measuring apparatus from an environment of the air duct to which the measuring chamber is exposed.

13. An air-mass measuring system for a vehicle, comprising:
an air-mass measuring apparatus for a vehicle, the apparatus including:
a support element;
an air-mass sensor for providing air-mass data, the air-mass sensor being disposed on the support element;
at least one further sensor for providing further sensor data, the at least one further sensor being disposed on the support element;
an evaluation circuit having a first input interface to receive the air-mass data, at least one second input interface to receive the further sensor data, and an output interface that includes a first wire connected to a source power voltage, a second wire connected to ground, and a third single shared data output wire, the evaluation circuit being disposed on the support element and being designed to provide the air-mass data and the further sensor data as bundled sensor data via the output interface by storing the air-mass data and the further sensor data and processing the stored air-mass data and the stored further sensor data to convert them into an integrated data element of a communications protocol, which is transmitted over the third shared single data output wire; and
a housing that has an electronics chamber and a measuring channel for conducting a gas and an electrical connection;
wherein:
the support element is disposed in the electronics chamber;
the air-mass sensor is inserted into the measuring channel;
the output interface is connected to the electrical connection via electric lines to make the bundled sensor data available at the electrical connection;
the air-mass measuring apparatus is disposed in an induction tract of a combustion engine of the vehicle and is connected via the electrical connection to a control unit of the vehicle; and
the integrated data element is transmitted as a signal voltage representing an amplitude-modulated or frequency modulated signal.

14. An air-mass measuring method for a vehicle, comprising:
receiving air-mass data via a first input interface of an evaluation circuit disposed on a support element, the air-mass data representing data provided by an air-mass sensor situated on the support element;
receiving further sensor data via at least one second input interface of the evaluation circuit, the further sensor data representing data provided by at least one further sensor situated on the support element;

storing the air-mass data and the further sensor data;
processing the stored air-mass data and the stored further sensor data to convert them into an integrated data element of a communications protocol; and
transmitting the integrated data element over a single shared data output wire of the output interface of the evaluation circuit, wherein the output interface includes the single shared data wire, a wire connected to a source power voltage, and a wire connected to ground;
wherein the integrated data element is transmitted as a signal voltage representing an amplitude-modulated or frequency modulated signal.

* * * * *